United States Patent [19]

Byler

[11] 4,186,746
[45] Feb. 5, 1980

[54] BODY WARMING DEVICE

[75] Inventor: William H. Byler, 804 Village La., Winter Park, Fla. 32792

[73] Assignee: William H. Byler and Thelma T. Byler, Trustees of William H. Byler Revocable Trust, Winter Park, Fla.

[21] Appl. No.: 870,012

[22] Filed: Jan. 16, 1978

[51] Int. Cl.$^2$ .............................................. A61F 7/00
[52] U.S. Cl. ..................................................... 128/403
[58] Field of Search ............................... 128/379–385, 128/399, 402, 403, 254, 24.1, 82.1; 126/263, 204, 207, 206; 150/2.1, 2.2, 2.3, 2.4, 2.5; 165/46; 220/301

[56] References Cited

U.S. PATENT DOCUMENTS

| | | | |
|---|---|---|---|
| 491,627 | 2/1893 | Yeoman | 128/402 |
| 1,264,666 | 4/1918 | Ljungstrom | 128/399 |
| 2,018,367 | 10/1935 | Lackenbach | 126/263 |
| 2,615,443 | 10/1952 | Sukacev | 126/263 |
| 2,850,006 | 9/1958 | Karpalo | 126/263 |
| 3,064,640 | 11/1962 | Donath | 126/263 |
| 3,175,558 | 3/1965 | Caillouette et al. | 128/403 |
| 3,450,127 | 6/1969 | Harwood, Jr. | 126/204 |
| 3,542,032 | 11/1970 | Spencer, Jr. | 128/399 |
| 3,545,230 | 12/1970 | Morse | 128/403 |
| 3,643,665 | 2/1972 | Caillouette | 128/403 |
| 3,763,622 | 10/1973 | Stanley, Jr. | 128/403 |
| 3,874,504 | 4/1975 | Verakas | 128/403 |
| 3,884,216 | 5/1975 | McCartney | 126/204 |
| 3,951,127 | 4/1976 | Watson et al. | 206/126 |
| 3,976,049 | 8/1976 | Yamashita et al. | 126/263 |
| 3,980,070 | 9/1976 | Krupa | 126/263 |
| 4,026,299 | 5/1977 | Sauper | 128/400 |

Primary Examiner—William E. Kamm
Attorney, Agent, or Firm—Pennie & Edmonds

[57] ABSTRACT

A portable body warming device is disclosed having a housing which encloses separately a water compartment and a salt compartment. The salt compartment has segmented chambers, each of which contains salt which reacts exothermically with water supplied by means of interconnecting tubes. Addition of the water to the salt is controlled such that the exothermic reaction is effected over a period of time and usefully serves to warm the body of a user. For use in emergency water immersion situations, an automatic double starting valve is disclosed.

11 Claims, 10 Drawing Figures

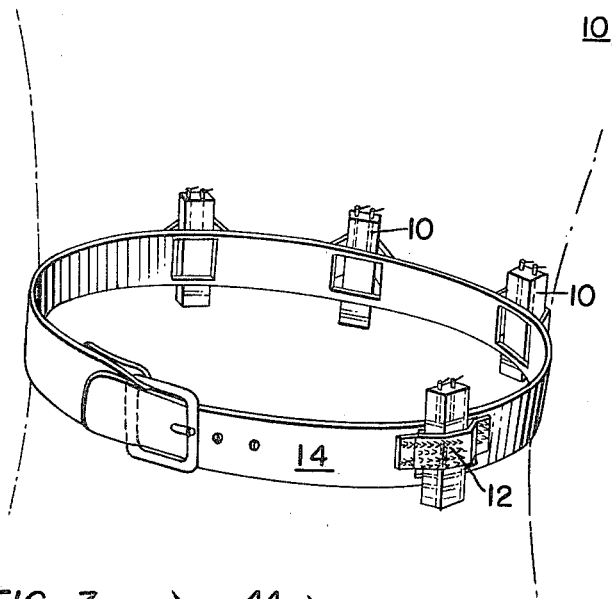
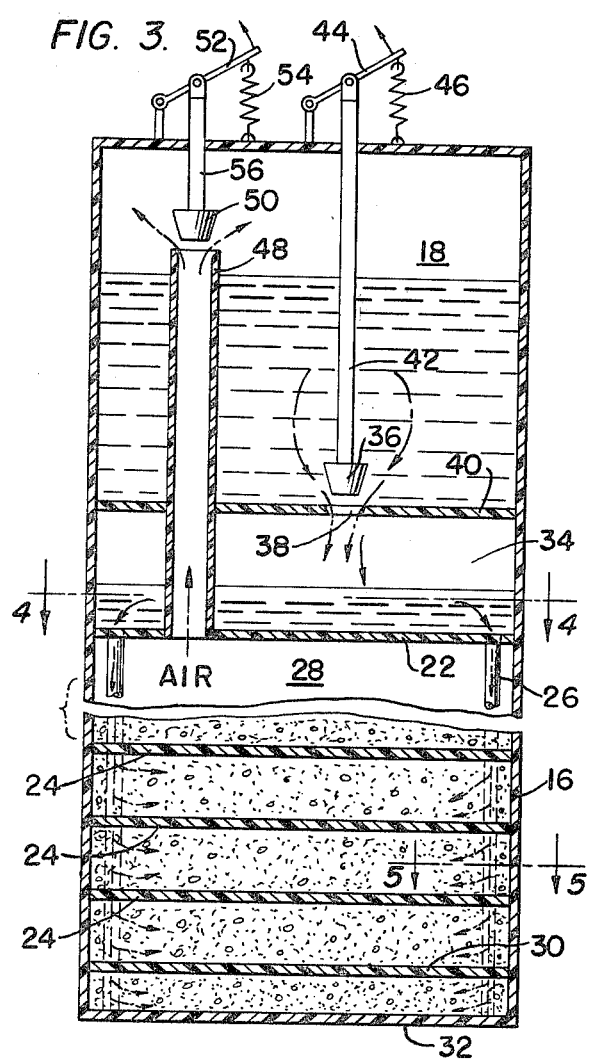
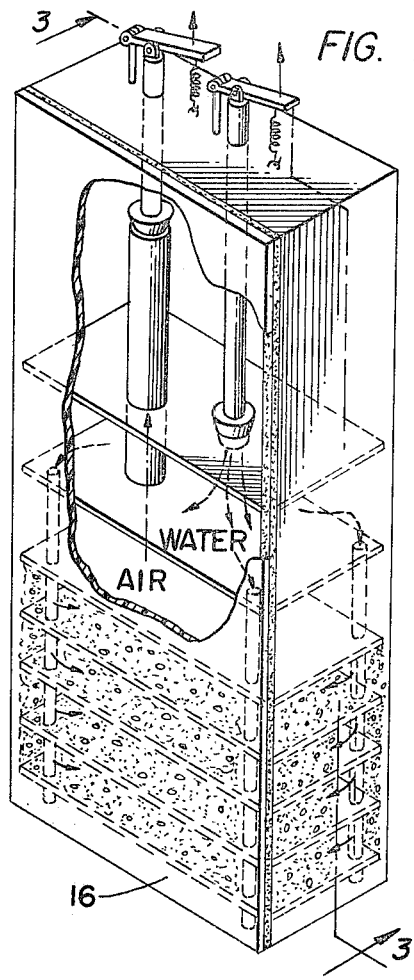
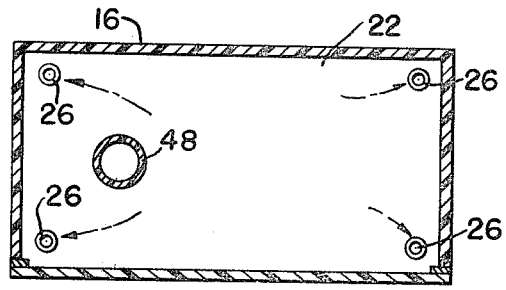
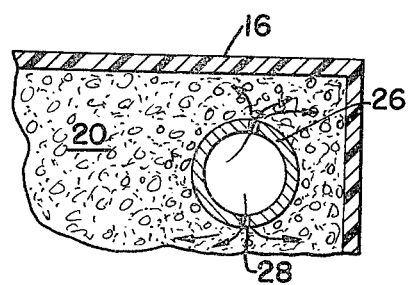

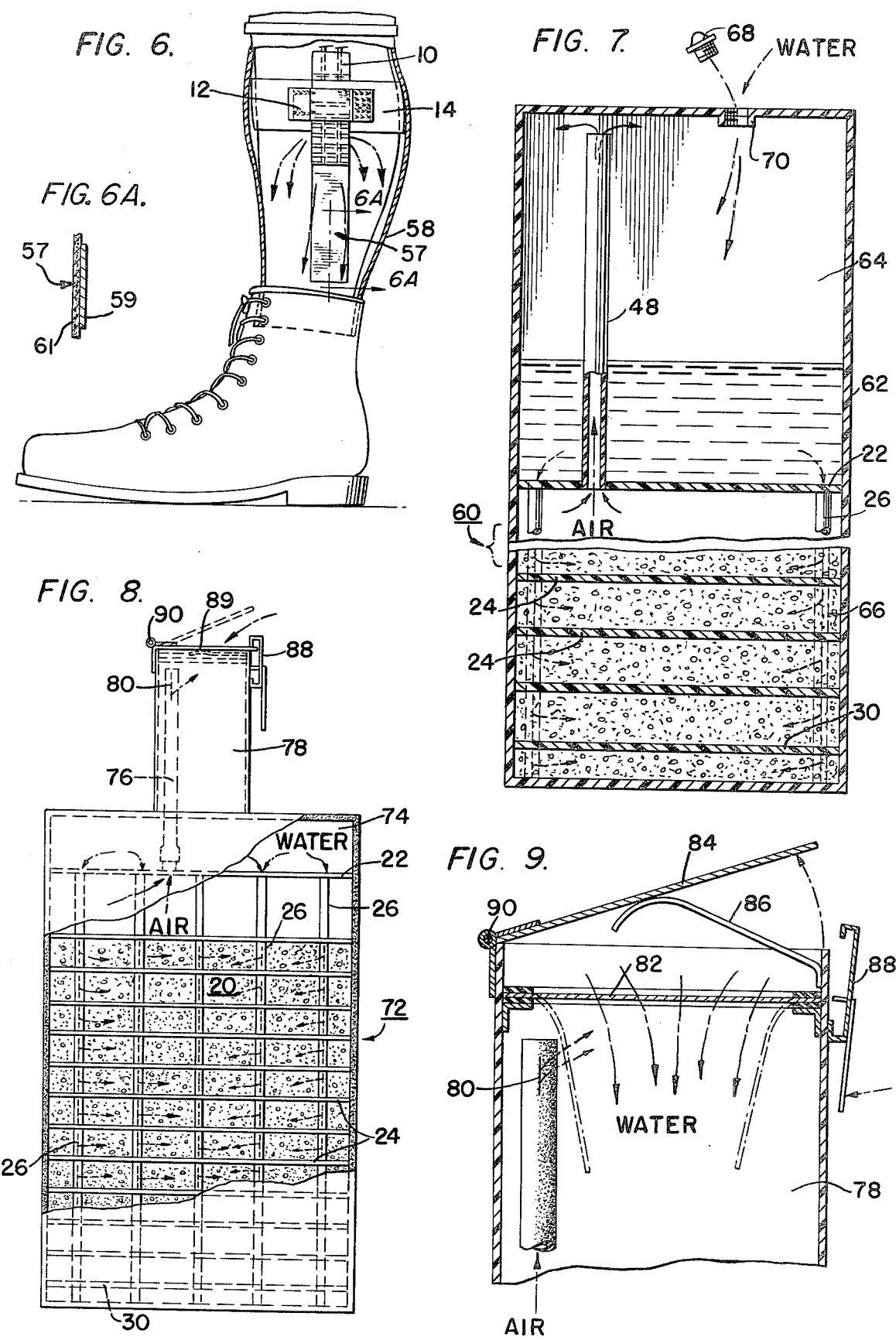

BODY WARMING DEVICE

BACKGROUND OF THE INVENTION

1. Field of the Invention

The present invention relates to a portable body warming device having means to controllably release heat by reaction of water with a dehydrated salt.

2. Description of the Prior Art

It is now recognized that many drownings are due to long exposure to cold water; for example, prolonged exposure in water as warm as 65° F. has resulted in loss of enough body heat to cause death. The need indicated here is a simple heat source which can operate safely under water and which will start operating automatically when immersed. Having developed a device to meet this need, I discovered that there is need for body warmers in many other situations as evidenced by the various devices offered to the market in recent years and by the growing demand. It was discovered also that each of these devices has limitations and deficiencies and that various embodiments of my invention could better serve the needs in many situations.

Body warmers presently available include electrical heat sources, heat sources based on use of a combustible fuel, and chemical heat generating systems.

Electrical heat generating sources suffer disadvantages in wet environments and become ineffective. Similar disadvantages are experienced with heat sources using combustible fuels. Electrical heat sources are also relatively expensive and require a battery which may be bulky and heavy. On the other hand, it is difficult to control the heat output of devices using combustible fuels.

Chemical heat generating systems of the prior art frequently have complex construction, require agitation in use, generate heat over a short period of time, or employ expensive or objectionable chemicals and none provides an automatic start feature on immersion in water. Prior art teachings have used salts such as calcium chloride, in reaction with water; viz., U.S. Pat. No. 3,643,665, U.S. Pat. No. 3,542,032, U.S. Pat. No. 3,874,504, and U.S. Pat. No. 3,175,558. However, these teachings require mixing the water with calcium chloride in bulk without agitation. This procedure results in salt caking with uncontrollable slow heat production after an initial burst. Encapsulation has been proposed and, even if feasible for calcium chloride, would increase the cost and would result in larger volume and weight per unit of heat. The present invention overcomes these problems and provides heat sources which provide controlled output over periods of hours.

SUMMARY OF THE INVENTION

Generally stated, the present invention provides a portable body warming device having a housing which contains a water compartment and a salt compartment.

Following are some features of the present invention:

(1) The salt compartment includes segmented chambers in stacked arrangement each having salt which reacts exothermically with water, this segmentation being the key to overcoming caking and allowing controlled, useful heat production over a period of hours;

(2) Use of a plurality of water conveyor tubes provide means for good distribution of water and nearly complete dissolution of salt;

(3) Means for controlling the rate of water flow by choice of tube opening size;

(4) Slotted tubes provide means for controlling level of introduction of water and avoid a need for an extra water head;

(5) Means for controlling distribution of heat by use of insulation and attached strips of heat conducting material;

(6) Means for opening the devices for insertion of salt, placement of selected tube opening caps, and emptying of salt solution; and (7) Double valve arrangement for the water immersion type embodiment which keeps salt dry during storage, the outer member of which opens automatically when the device is mounted on the body of a user such that the inner member will open automatically on immersion in water, the outer member being operable manually by a user upon demand.

The principal categories of the present embodiments are:

(1) The simplest embodiment which is carried dry, water being added at the time heat is desired, no valves being needed.

(2) The embodiment which is carried charged with both salt and water and operated by valves as desired.

(3) The embodiment for use under water with automatic double valve.

Convenient sizes of chemical chambers for various uses may range from about 20 ml. for ear muffs to about 800 ml. for water immersion type, sizes for pocket warmers and leg-foot warmers being intermediate.

It is an object of this invention to provide a body warming device having a controllable heat output regulated by the rate of water addition to a salt which reacts exothermically during hydration.

It is also an object of this invention to provide a body warming device which does not require agitation to effect useful heat generation over long periods.

It is a further object of this invention to provide a body warming device where the spent heat source may be reclaimed by the user.

It is another object of this invention to provide a body warming device which operates under water and which is activated automatically on contact with water.

BRIEF DESCRIPTION OF THE DRAWINGS

FIG. 1 is a perspective view of the body warming devices of the present invention secured to a belt for attachment about the waist of a user's body, the sizes not being to scale.

FIG. 2 is a perspective view, partially broken, and illustrating a body warming device of the present invention.

FIG. 3 is a front sectional view taken along lines 3—3 of the body warming device of FIG. 2.

FIG. 4 is a sectional view taken along lines 4—4 of the body warming device of FIG. 3.

FIG. 5 is a partial sectional view taken along lines 5—5 of the body warming device of FIG. 4 and illustrating a means for water transfer to effect heat generation.

FIG. 6 illustrates the body warming device of the present invention secured to a belt attached about the calf of a user's body, FIG. 6A being a sectional view of lines 6A—6A.

FIG. 7 is a front elevational view taken in half section and illustrating a simple valveless embodiment of the body warming device of the present invention.

FIG. 8 is a front elevational view taken in half section and illustrating another embodiment of the body warming device of the present invention.

FIG. 9 is a partial front elevational view taken in half section and illustrating a further embodiment thereof.

DESCRIPTION OF THE PREFERRED EMBODIMENTS

Referring to the drawings wherein similar elements are identified by like numerals, FIG. 1 illustrates body warming device 10 secured by retaining band 12 onto belt 14 which may be secured about a user's waist. Although not illustrated to scale, warming device 10 may be positioned directly in contact with the body, i.e., on the inner side of the belt, or, alternatively, the belt may include cut-out portions as illustrated.

FIGS. 2 to 5 show body warming device 10 in greater detail having housing 16 within which is disposed a water reservoir compartment 18 and a salt compartment 20 separated by divider 22. The salt compartment 20 includes a plurality of spacing members 24 which separate the salt into segmented chambers. This construction grew out of the discovery that the salts most useful for heat production tend to cake as water is added, thus, greatly reducing surface area interfacing with water and sharply decreasing rate of dissolution. By limiting layer thickness and weight per unit, caking of desirable salts can be controlled. Spacing members 24 are disposed uniformly one from another except for spacing member 30 which is disposed closer to bottom 32 of housing 16. This is desirable since experiments reveal a greater tendency toward caking of salt in the bottom layer. Actual spacing may vary with kind and form of salt used, but, for example, experiments with calcium chloride pellets indicate preferred spacing of about 10 to 15 mm., the bottom spacing being about 5 to 8 mm., the objective being to promote more complete reaction of water with salt. The spacing members may be attached to the housing at a few points sufficient for stability but leaving space around the periphery such that salt pellets or flakes are retained while water is free to flow. With such a fixed shelf system, one side of the housing covering the salt chamber is a removable gasketed panel which provides access for filling and emptying. Alternatively, a complete insert shelf can be filled, then inserted from the bottom with the aid of a filling case which can be inserted with the shelves then slid out, a bottom removable panel being used in this case.

Water tubes 26 are placed at or near the housing walls and extend from the divider 22 to near the bottom of the salt compartment 32. The tubes are placed so that all salt is within a maximum of 2 to 4 cm. of a tube, the objective again being to promote more complete reaction of water with salt.

In operation, the device is activated by lifting lever 44 which lifts plug 36 by rod 42 from port 38 in platform 40 allowing water to flow from reservoir 18 into distributor compartment 34 from which it flows into water conveying tubes 26 and into the salt chamber through the open ends near the bottom; lever 44 is spring biased 46 in closed position but can be set in open position. Rate of flow of water is variable and controlled by friction caps with varied opening sizes which fits into tops of the water conveyor tubes. These tubes may have solid walls for use in the water immersion type where water head is not a problem. Since, for example, concentrated calcium chloride solution has a density of about 1.5, there must be a head of about 1.5 times the height of the salt chamber if solid wall tubes are used. By using tubes with a full length slot of such width, on the order of 1 mm. or less, that water is retained by surface tension so that it flows to the bottom or to the existing solution level, the overall size of the device can be substantially smaller in relation to heat production capacity.

The distributor compartment 34 is needed for this valve-operated embodiment to promote relatively uniform distribution of water to the various water conveyor tubes so that an essentially uniform head and, thus, uniform flow rate can be maintained as the device becomes tilted during operation.

The valve 36-38 serves only to retain the water until heat is wanted and could not adequately control rate of heat production. The partition 40 serves to support the valve and to provide the distribution chamber 34 which distributes water to all conveyor tubes 26 where flow rate is controlled by choice of opening size. Thus, the distribution chamber tends to promote maintenance of uniform head to the various tubes during operation, but during the last stages of a run, tilting would tend to favor tubes on the low side. Although in normal practice direction of tilt will be random, the devices such as those of FIG. 2 and FIG. 7 with their limited water supply should be mounted in vertical or near vertical position. If flow rate were controlled by valve 36-38 at times when water is low in compartment 34, tilting the device could result in no water supply for some tubes. Such a distributor compartment is not needed for the embodiment of FIG. 7 since no valve is used. Also, for the embodiment of FIG. 8 (water immersion type), the distributor function is served by a simple full cross-section extension of the main body of the housing.

An air relief tube 48 is obviously needed to allow air to escape from the salt compartment 28 as water flows in. This is normally closed by plug 50 on rod 56 to prevent water vapor access to the deliquescent salt and is activated by lever 52 biased in the closed position by spring 54 and may be set in open position, this being done at the same time lever 44 is set in the open position.

Regarding choice of salt, there are many which are known to produce large amounts of heat through hydration but few which are suitable for purposes of this invention. Important considerations are safe handling, cost, adaptability to a system for controllable delivery of heat over long periods, device volume required per unit of heat produced, simplicity of reclaim, etc. Magnesium sulfate, magnesium chloride, and calcium chloride may be used. However, calcium chloride is the preferred salt since it is well known as an innocuous salt, it is available in favorable pellet form at low cost, it can be reclaimed to anhydrous state by simple heating, it has high bulk density and can produce relatively high output per unit volume, and it is particularly suited for use in these described devices for controllable efficient operation.

It has further been found that calcium chloride when used as described herein without agitation exhibits the surprising property of forming a complex solution-suspension (probably partially colloidal) whereby complete dissolution occurs when weight of water roughly equals weight of anhydrous salt whereas a true saturated solution is only 40% salt. Tests show that addition of water with agitation produces more heat but that a 53% larger device size is needed to produce 35% more heat. Therefore, in view of the low cost of calcium chloride and simplicity of reclaim, this special property is advantageous since it results in more heat per unit volume.

In FIG. 5, outlets 28 are illustrated in water tube 26 and may appear as slots or openings disposed as desired to convey water to as great an area of salt as possible for maximum efficiency of the device.

FIG. 6 illustrates an embodiment usage of the present body warming device 10 conveniently secured by belt 14 and strap 12 about the calf of a user. In order to permit more effective application, body warming device 10 may include a containing envelope 58, such as foil or like material, to entrap the heat. Alternatively, a heat conductive strip 57 may be attached to the device for conduction of heat to additional areas of the body. Heat conductive strip 57 may be laminated such as illustrated in the partial sectional view 6A with a conductive strip 59 formed of known heat conductive metals, for example, and insulation strip 61 also formed of known insulation materials. One example of a heat conductive strip would be a lamination of aluminum foil and cloth covering.

FIG. 7 shows embodiment device 60 formed of enclosure 62 which is suitable to carry and is charged with salt in compartment 66 but to which water is added in compartment 64 at the time heat is wanted. Water is introduced into compartment 64 simply by opening plug 68 from inlet 70. Since water flow rate is controlled by the size of the opening in the friction caps which fit into the tops of water conveyor tubes 26, no valve is needed. Also, no closure is needed for air escape tube 48 since no water is present during the period prior to operation. The water conveyor tubes are advantageously slotted to minimize water head and, therefore, size of the water compartment. Obviously, the full charge of water need not necessarily be added at one time.

FIGS. 8 and 9 illustrate embodiment device 72 which is particularly designed to immersion in water and to provide heat in immersion emergency situations. Here, again, water is not present prior to operation, so no internal valve is needed and the water flow rate is controlled by caps at the tops of tubes 26 which may be slotted but need not be because water head is not a problem. Water distribution chamber 74 serves its purpose while chamber 78 need not be as wide because its purposes are to provide a lower pressure region which allows operation of a simple slit 80 in rubber valve 76 which allows air to escape while preventing ingress of water, and to support the automatic double valve illustrated in detail in FIG. 9. The water rupturable membrane 82 may be prepared using a variety of available materials known to the art. Water-soluble materials are not ideal because they could fail to provide secure closure on long exposure to moist air. The spring 86 provides pressure which allows use of a material such as sized paper which is secure until well wetted, within cover 84 pivotably mounted about pin 90. Cover 84 is released by cover release catch 88.

These devices may be carried in pockets, incorporated in wearing apparel, or secured to the body of the user by any convenient means such as belt or tape. Effectiveness is obviously improved when in close contact with the body and this is especially important in the water immersion situation where heat can be dissipated through flow of water. Therefore, for this purpose, a special insulated belt or vest with inward-facing pockets and water ingress opening only on the top side will provide maximum efficiency. Obvious means can be provided for automatic opening of the outer valve during the mounting operation.

It will be apparent to those skilled in the art that numerous changes and variations may be made in the description of the present embodiments without departing from the essence of the present invention. Accordingly, it is intended that the description of the present invention and accompanying drawings are to be interpreted for purposes of illustration rather than as limiting practice of the present invention.

What is claimed is:

1. A body warming device which comprises in combination:
    (A) a housing containing a water compartment and a salt compartment, said salt compartment having segmented chambers in stacked arrangement each containing salt which reacts exothermically with water;
    (B) a plurality of water conveying tubes interconnecting the water compartment and the salt compartment, said tubes extending between said water compartment and the lowest of said segmented chambers to deliver water first to the lowest of said chambers then to higher chambers in succession;
    (C) an air relief tube interconnecting the salt compartment and the water compartment; and,
    (D) means for controllably supplying water from the water compartment to the salt compartment.

2. The body warming device of claim 1 wherein the water conveying tubes are slotted.

3. The body warming device of claim 1 wherein an opening is provided in the water compartment for introduction of water whenever heat is desired.

4. The body warming device of claim 1 wherein the water compartment is partitioned to provide an upper water storage chamber and a lower water distribution chamber, the partition having an opening with valve control, the air relief tube having a valve closure, said valve control and valve closure controlled by control means accessible from outside the housing.

5. The body warming device of claim 1 wherein an upper opening in the water compartment is closed by a water rupturable membrane which weakens on immersion in water and allows water to enter.

6. The body warming device of claim 5 including a water-tight closure provided over the water rupturable membrane, means for mounting said closure on said housing, and opening means operable both manually and automatically when the device is mounted for use.

7. The body warming device of claim 5 including spring means, said spring means supported by said housing and extending both along and in contact with said water-rupturable membrane thereby to spring-load said water-rupturable membrane.

8. The body warming device of claim 1 including heat conducting means, said heat conducting means attached to and extended beyond the situs of said housing thereby increasing the distribution of heat to other parts of the body.

9. The body warming device of claim 1 having means for securing to the body of the user and for insulating against loss away from the body.

10. The body warming device of claim 1 wherein said air relief tube includes a valve closure for preventing ingress of water to said salt compartment while permitting escape of air from said salt compartment.

11. The body warming device of claim 10 wherein said valve closure includes a slit through a wall and along said tube.

* * * * *